United States Patent [19]
Cho

[11] Patent Number: 5,823,191
[45] Date of Patent: Oct. 20, 1998

[54] CONDOM

[76] Inventor: Gill-ho Cho, #207, Mokdong-Shinsigaji Apt. 707-dong, 925, Mok-dong, Yangchon-gu, Seoul, Rep. of Korea

[21] Appl. No.: 808,068

[22] Filed: Feb. 28, 1997

[30] Foreign Application Priority Data

Nov. 5, 1996 [KR] Rep. of Korea ................. 96-52156

[51] Int. Cl.⁶ ............................................. A61F 6/04
[52] U.S. Cl. .................................... 128/844; 128/918
[58] Field of Search ................... 128/842, 844, 128/918; 604/347–353

[56] References Cited

U.S. PATENT DOCUMENTS

| | | | |
|---|---|---|---|
| 3,037,508 | 6/1962 | Friedman | 128/844 |
| 3,648,700 | 3/1972 | Warner | 128/844 |
| 3,759,254 | 9/1973 | Clerk | 28/844 |
| 4,821,742 | 4/1989 | Phelps | 128/844 |
| 5,421,350 | 6/1995 | Friedman | 128/844 |

Primary Examiner—Michael A. Brown
Attorney, Agent, or Firm—Dann, Dorfman, Herrell and Skillman; Henry H. Skillman

[57] ABSTRACT

An improved condom includes a small sack for collecting semen, a condom sack not compressing but surrounding the glans in wearing, a supporting portion extending from the rear of the condom sack, and a string, band or tear strips for removing the condom. The supporting portion is shorter than a half of the erect penis in length, slightly thicker than the condom sack in thickness, compressing the penis only enough to prevent the condom from slipping out, so that, in use, wearer feels comfortableness and cleanliness not by disturbing the blood circulation in the spongeness structure of the glans, and also, it is easy to put on and take off the condom, and provide a more contact of skin during sexual intercourse with comfortableness and satisfaction. Further, it is easy to reuse the once used condom just by washing or disinfection and then fold it once. Therefore the present invention is environmentally friendly in view of saving resources and preservation of environment.

13 Claims, 3 Drawing Sheets

FIG. 1 (PRIOR ART)
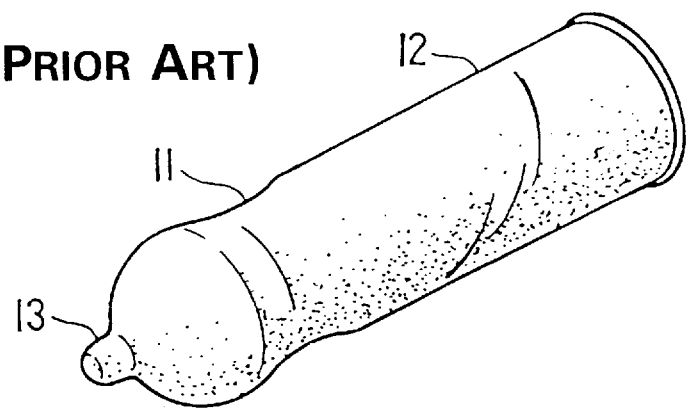
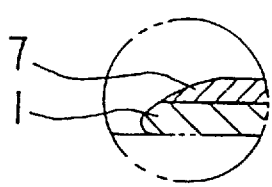
FIG. 2A
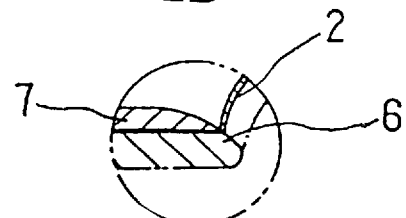
FIG. 2B
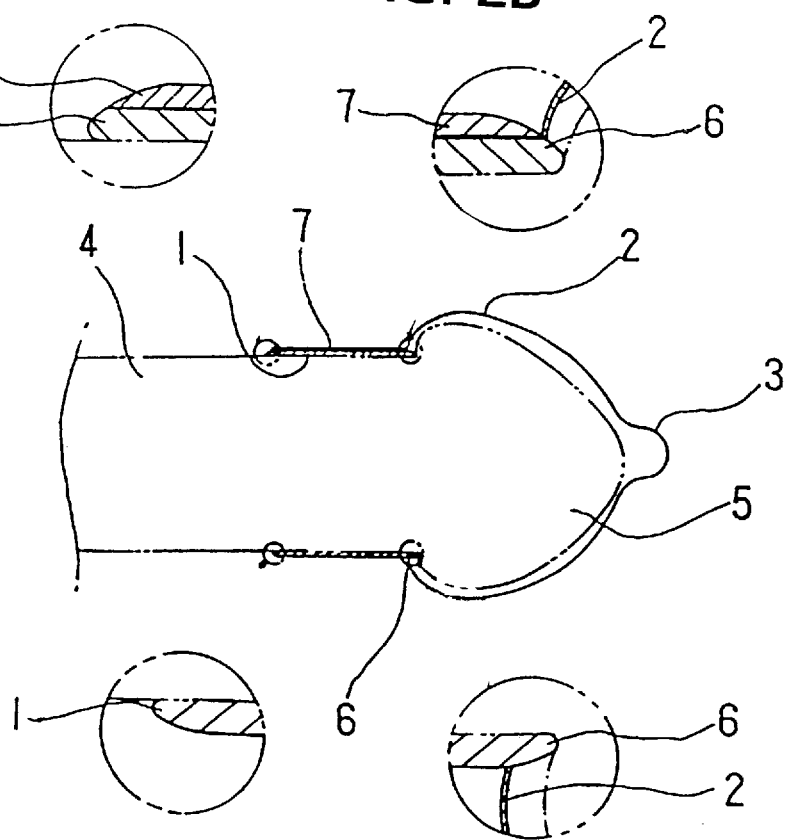
FIG. 2
FIG. 2C
FIG. 2D

CONDOM

BACKGROUND OF THE INVENTION

1. Field of the Invention

The present invention relates in general to condoms and, more particularly to an improved condom made of latex or silicone in which the thickness of a supporting portion forms thickly and the length forms shortly so that can put on and/or take off a condom easily and can give a comfortable feeling in wearing.

2. Description of the Related Art

As well known to those skilled in the art, several types of condoms have been used for contraception and prevention of diseases such as venereal disease, since condom has been firstly proposed by Dr. Condon in 18th century. In addition, the demand for the condom has been increased more-or-less in accordance with the changes of times and society. Recently, the demand is soaring relating to protection for contagions of incurable diseases such as AIDS.

FIG. 1 is a perspective view showing a conventional condom. Conventionally, a condom consists of a condom body 12, a small sack 13 for collecting semen, and a recess portion 11 as shown in this view. The recess portion 11 protect a slightly depressed part on the rear concave portion of the glans when the user is wearing a condom, and a small sack 13 as a semen collector protruding from the body 12. The condom body 12 covers the penis completely in order to prevent the semen from leaking and secure the condom on the penis without slipping therefrom. This conventional condom is generally made of latex or silicone and covered with lubricant or the like to reduce the frictional coefficient on the vaginal wall.

In case that a user uses the condom, at first, the user put a rolled condom close to penis and then unfolds completely with care to prevent air from entering into the condom. However, in the conventional condom, there are some drawbacks as follows;

One of the drawbacks of the conventional condom is a considerable difference in feeling between wearing and not wearing condom, because the condom body presses the penis tightly by which the wearer feels somewhat stuffy and uncomfortable feeling as the blood circulation in the glans is disturbed. This is basically caused by the acute sense of the glans of penis having a spongeness structure. In a conventional condom, the condom body covers the penis as close as possible in wearing to prevent the secreted semen in the small sack from leaking toward the rear of the penis.

In addition, a conventional condom is inconvenient to put on and taken off. Further, it tends to slip from the penis during sexual intercourse. In case of putting on the condom, the wearer smears his fingers with a wax, lubricant or the like applied over the outer surface of the condom. Consequently, the wax lubricant is smeared to the outer surface of the penis as well as the inner surface of the condom by the lubricant smeared fingers, therefore, the wearer feels uncomfortableness because the lubricant blocks the pores in the skin of the glans, and also, the condom is easy to slip out of the penis during sexual intercourse as the frictional force between the inner surface of the condom and the penis decreases.

Especially, in this conventional condom, it has been very difficult to reuse the once used condom. There have been known some methods for reuse of the once used condom, but those are very cumbersome because several difficult steps are required such as washing, drying and folding up like the original state. If it is not folded up after drying, any special care is required in the course of wearing in order that no air is introduced between the penis and the inner side of the condom. Therefore, in a conventional condom, the reuse is nearly impossible and which is undesirable in view of the saving of resources and the preservation of environment.

SUMMARY OF THE INVENTION

It is, therefore, an object of the present invention to provide a condom in which the above problems can be overcome.

One object of the present invention is to provide a condom which can give a comfortable feeling in wearing in a manner such that the glans is not compressed tightly.

Another object is to solve a problem in the conventional condom which is inconvenient to put on and/or take off and is slipped out of the penis during sexual intercourse.

A further object is to provide a condom can be reused as well as to provide comfortableness and satisfaction with maximizing the skin contact area in sexual intercourse.

According to the present invention, the foregoing and various objects, advantages are attained by providing an improved condom comprising two part, that is, a condom body surrounding glans having a small sack for collecting semen therein, and a supporting portion of which length is shorter than a half of the penis, in a manner of compressing the penis enough not to slip out of the penis.

In the above improved condom, the supporting portion which covers a body of the penis excluding the glans (will be referred as the penis body hereinafter) is relatively short compared with the prior art since the conventional condom body portion has caused rather hard to put on and/or take off. Further, the thickness of the supporting portion forms thicker than the condom body, by which the supporting portion compresses penis constantly only to the extent that the condom does not slip out of the penis not by compressing the glans during sexual intercourse.

Furthermore, on the supporting portion of the present invention, plurality of aperture which is regularly or irregularly arranged may be formed to assure ventilation and to maximize the skin contact area in sexual intercourse. Which is desirable to have largest possible aperture rate if it does not cause a change in original function of the supporting portion.

Moreover, the present invention can be further provided with one or more auxiliary taking-off means on the supporting portion for assisting to remove it after using.

Additional objects, advantages and novel features of the invention will be set forth in part in the description which follows, and in part will become apparent to those skilled in the art upon examination of the following or may be learned by practice of the invention.

The objects and advantages of the invention may be realized and attained by means of the instrumentalities and combinations particularly pointed out in the appended claims.

BRIEF DESCRIPTION OF THE DRAWINGS

FIG. 1 is perspective view showing conventional condom in the prior art;

FIG. 2 is a cross sectional view showing a condom of one embodiment of the present invention;

FIG. 2A is an enlarged fragmentary sectional view of the top of the outer end of the supporting portion of the condom in FIG. 2;

FIG. 2B is a fragmentary sectional view of the top of the inner end of the condom in FIG. 2;

FIG. 2C is a front sectional view of the bottom of the outer end of the supporting portion of the condom in FIG. 2;

FIG. 2D is a front sectional view of the bottom of the inner end of the supporting portion of the condom in FIG. 2;

DETAILED DESCRIPTION OF THE PREFERRED EMBODIMENTS

Figure 3A:
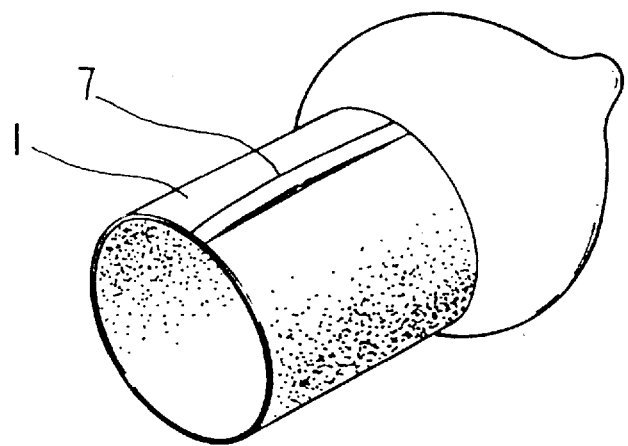
FIG. 3A is a perspective view showing supporting portion of the condom in FIG. 2.

One embodiment of the present invention will now be described with references to the drawings hereinafter.

Referring to FIG. 2, a condom comprises a small sack 3 for collecting the secreted semen therein, a condom sack 2 surrounding the glans 5, a supporting portion 1 extending from the rear portion of the condom sack 2. As shown in FIG. 2, the supporting portion 1 forms shorter in length and also slightly smaller in diameter compared with the erect penis with compressing the penis body 4 constantly. Desirably, the length and the diameter of the supporting portion is within 15 to 25 mm and 20 to 30 mm, respectively. The thickness thereof is slightly thicker than the condom sack 2, desirably about 1 mm, having a less elasticity than the condom sack 2. One end of the supporting portion 1 forms rounded in shape for touching the penis gently. A lever 6 having a rounded end is further provided between the supporting portion 1 and the condom sack 2, protruding toward the rear concave portion of the glans 5. Desirably, the length of the lever 6 is about 1 mm.

The condom sack 2 has a glans-like shape and is nearly equal to the size of glans 5 to cover enough the glans 5 in such a state of a maximum diameter about 35 to 45 mm. The lever 6 forms a minute gap between the condom sack 2 and the rear concave portion of the glans 5.

Further, the supporting portion 1 can be provided with one or more auxiliary taking-off means for assisting to remove the once used condom.

Referring to FIG. 3A, a supporting portion of a condom according to one embodiment of present invention is shown. In such a case, a taking-off means such as string shape 7 is provided in a state that only both ends thereof is fixed to the supporting portion 1, while the middle portion thereof is free from the supporting portion. However, either of one end of the taking-off means may be fixed to the supporting portion. One or more taking-off means may be provided in such a manner that one or more pairs forms symmetrically each other on the upper side and lower side or left side and right side of supporting portion. The taking-off means can be also formed with a band shaped type having a predesignated width thereof.

Figure 3B:
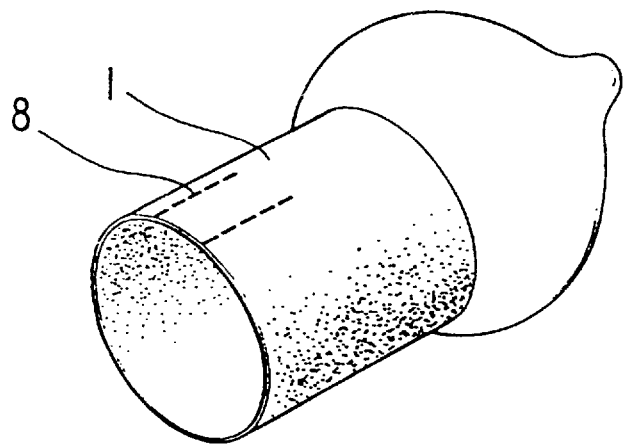
FIG. 3B is a perspective view showing supporting portion of a condom in another embodiment of the present invention.

According to another preferred embodiment of the present invention, FIG. 3B, shows a supporting portion of a condom having two perforated line 8, tear strips, regularly perforated from the end of the supporting portion 1 formed in a direction of penis body 4 in predesignated length. Thus formed lines 8 can be used by being pulled apart from the supporting portion 1 as an auxiliary taking-off means for assisting the condom-off operation when the taking-off means such as string shape 7 is broken. The width and length of the perforated lines 8 is desirably about 5 mm and 10 mm, respectively and if necessary, these perforated lines 8 can be provided one more pairs in a manner of symmetrically on the supporting portion.

Figure 4:
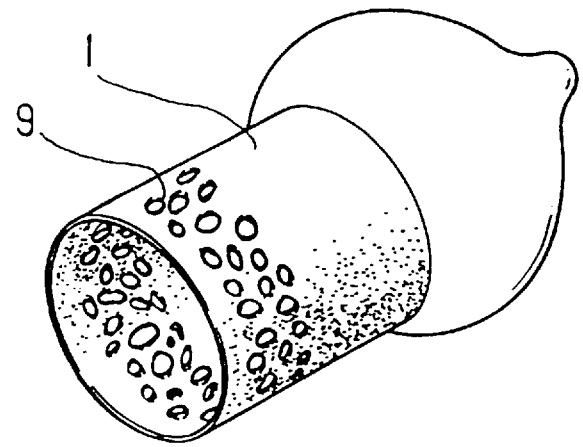
FIG. 4 is a perspective view showing a supporting portion of a condom in further embodiment of the present invention.

Referring to FIG. 4, a supporting portion 1 according to a further embodiment of present invention is provided, which has a plurality of aperture 9 over the supporting portion 1 to assure ventilation and to maximize the possible skin contact area in sexual intercourse. These apertures 9 form desirably to have largest possible aperture rate if it does not cause to change in original function of the supporting portion 1. In order to assure the largest possible skin contact area either regular or irregular apertures in arrangement and shape may be available.

Especially the condom body, supporting portion and taking-off means are desirably made of latex or silicone which is generally used as a material of the operating gloves for doctors, so that it is possible to reuse just by washing or disinfection after being used once.

In use the condom of the present invention, the supporting portion 1 will compress the penis body 4 with a constant pressure and the semen leaking from the small sack 3 be held in a gap which is formed by the lever 6 between the condom sack 2 and the rear concave portion of the glans 5 whereby no leakage of semen out of condom happen. Consequently, the condom sack does not compress tightly, so that the wearer can feel comfortable not by disturbing the blood circulation in the spongeness structure of the glans, and further the condom does not slip out from the penis during sexual intercourse since the supporting portion 1 compresses the penis body 4 with a constant pressure, while the lever 6 pushes like an anchor the rear concave portion of the glans 5 slightly.

In addition, the relatively short supporting portion enables putting on and/or taking off the condom to be easily and simply and the wearer feels comfortableness and cleanliness not by blocking the pores in the skin of the penis because the lubricant does not smears to the outer surface of the penis. It is also considerably easy to reuse just by washing or disinfection and then fold it once. Therefore, the present invention is environmentally friendly in view of saving of resources and preservation of environment.

Usage of the condom according to the present invention will be described hereinafter with reference to FIGS. 5A to 5D.

Figure 5A:
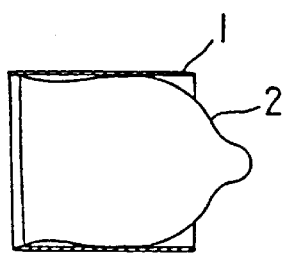
FIGS. 5A, 5B, 5C, 5D is a cross sectional view showing successive steps for putting on and/or taking off a condom according to the preferred embodiment of the present invention.
Figure 5B:
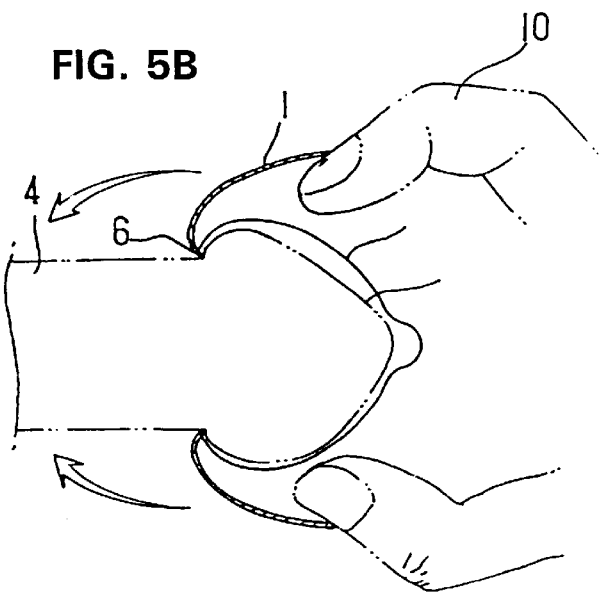

FIG. 5A shows a non used condom in which the supporting portion 1 is turned inside out to surround the condom sack 2. In other words, the condom is supplied with packed in a case where the cylindrical supporting portion 1 surrounds the condom sack 2.

The first step for using a condom is to insert a thumb and an index finger into a space between the supporting portion 1 and condom sack 2, put an opening of the condom sack 2 to the glans 5, and, then, push the supporting portion 1 till the glans 5 is completely covered. Next step is to turn over the supporting portion 1 in the direction of arrow shown in FIG. 5B. The above two steps are similar to being put operation gloves on the doctor's hands by a nurse in the operation room. At the time, the lever 6 formed at the supporting portion 1 works like lever by being put the concave portion of the rear of the glans 5 and thus the supporting portion 1 is turned over with ease. This method enables the lubricant covering the outer surfaces of the condom sack 2 and the supporting portion 1 not to smear the inner surface of the supporting portion 1, therefore, sufficient frictional force between the supporting portion 1 and the penis body 4 does not decreased, and also, the wearer feels comfortableness and cleanliness not by the lubricant blocks the pores in the skin of the penis.

Figure 5C:
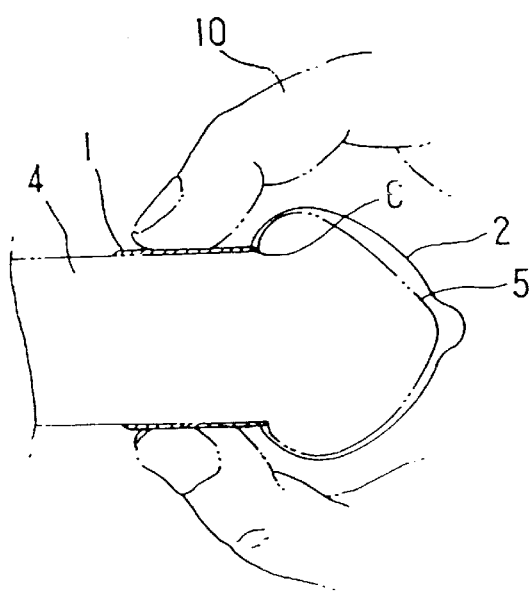
Figure 5D:
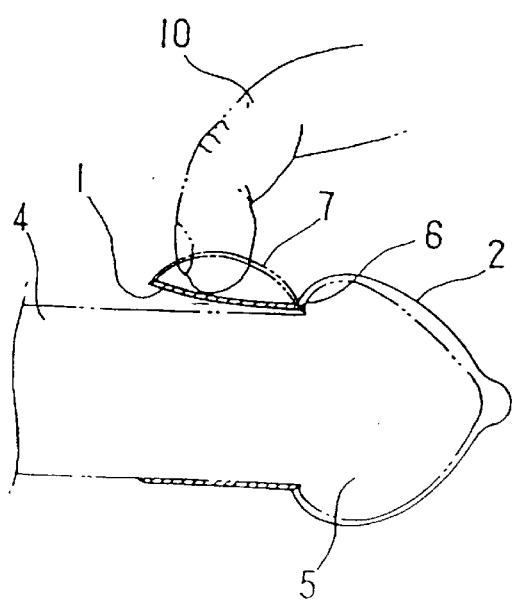

FIG. 5C shows the state that wearing is completed.

After using, the once used condom can be easily removed from the penis just by picking up the auxiliary taking-off means 7 such as a string band shape or the like with a index finger from the supporting portion 1 and pulls it forward.

As aforementioned a condom according to the present invention comprises two parts, that is a condom body surround glans having a small sack 3 for collecting semen therein, and the supporting portion 1 extending from the rear portion of the condom sack 2. The said supporting portion 1 is shorter than a half of the erect penis in length and slightly thicker than the condom sack 2 in thickness, compressing the penis enough to prevent the semen of the small sack 3 from leaking to the outside of the condom. In use of a condom according to the present invention a user can feel comfortableness and the condom sack 2 is secured safely in a state of without neither slipping out nor compressing the glans 5 during sexual intercourse since the supporting portion 1 compresses the penis body 4 with a constant pressure, while the lever 6 pushes like an anchor the rear concave portion of the glans 5 slightly. The relatively short supporting portion 1 enables putting on and/or taking off the condom to be easily and simply, and it is considerably easy to reuse the once used condom just by washing or disinfection and then fold it once.

Thus the present invention is environmentally friendly in view of saving resources and preservation of environment.

Moreover, the present invention can provide comfortableness and satisfaction with maximizing the skin contact area in sexual intercourse by further comprising of the plurality of apertures over the supporting portion 1.

The present invention has been described above with reference of the preferred embodiments thereof. It will be understood, however, that the invention in not restrained by the described embodiments and many modifications and variations can be made by those skilled in the art. All of the modifications and variations are incorporated within the scope of the appended claims.

What is claimed is:

1. An improved condom comprising:
   a small sack for collecting semen therein;
   a condom sack surrounding the glans in wearing; and
   a supporting portion extending from the rear of said condom sack;
   wherein said supporting portion is shorter than a half of the erect penis in length and thicker than said condom sack in thickness, compressing the penis enough to prevent the condom from slipping out and including one or more auxiliary taking-off means for assisting the condom off operation;
   said taking-off means having an elongated shape;
   both ends of said taking-off means being fixed to the supporting portion, leaving the middle portion thereof to be free from said supporting portion.

2. The improved condom according to claim 1, said supporting portion forms cylindrically in shape within 15 to 25 mm in length, 20 to 30 mm in diameter and 1 mm in thickness.

3. The improved condom according to claim 1, said auxiliary taking-off means comprising a string shape having at least one end fixed to one end of said supporting portion.

4. The improved condom according to claim 1, said auxiliary taking-off means comprising a band shape having at least one end fixed to one end of said supporting portion.

5. The improved condom according to claim 1, said taking-off means being coextensive in length with said supporting portion and having its ends fixed to opposite ends of the supporting portion, leaving the middle portion thereof to be free from said supporting portion.

6. The improved condom according to claim 1, wherein one end of said auxiliary taking-off means includes one pair or more perforated lines for tear strip from the end of said supporting portion in the direction of the penis body, said lines having a predesignated space therebetween and a predesignated length.

7. The improved condom according to claim 6, said predesignated space is 6 mm and said predesignated length is 10 mm.

8. The improved condom according to claim 1, said condom is further comprised of a lever which is extended from a contact point of said condom sack and one end of said supporting portion toward said condom sack by about 1 mm.

9. The improved condom according to claim 1, said supporting portion includes a plurality of apertures thereon.

10. An improved condom for application to a penis having a body and a glans joined to the front of the body by a rear concave portion of the glans, comprising:
    a condom sack having for enclosing the glans of the penis having a semen chamber formed integrally at its front;
    a generally cylindrical supporting unit connected to a rear end of said condom sack, having length shorter than a half of the erected penis and a thickness more than said condom sack; and
    taking-off means separate from said supporting unit, extending along the supporting unit and having both ends fixed to said supporting unit,
    the rear end of said condom sack being connected to the exterior of said supporting unit spaced from the front end of said supporting unit by a predetermined distance, whereby a lever is provided to form a predetermined space between a rear portion of said glans and the rear end of said condom sack.

11. The improved condom of claim 10, wherein said taking-off means is an elongated member extending along the length of said supporting unit.

12. The improved condom of claim 10, wherein said taking-off means is connected to the rear end of said supporting unit by a pair of cut lines parallel each other and having a predetermined spacing and length.

13. The improved condom of claim 10 including a plurality of air vents formed at the surface of said supporting unit.

* * * * *